United States Patent
Tanigawa et al.

(10) Patent No.: US 11,071,525 B2
(45) Date of Patent: Jul. 27, 2021

(54) ULTRASONIC DIAGNOSTIC APPARATUS AND METHOD

(71) Applicant: General Electric Company, Schenectady, NY (US)

(72) Inventors: Shunichiro Tanigawa, Tokyo (JP); Takuma Oguri, Tokyo (JP)

(73) Assignee: General Electric Company, Schenectady, NY (US)

(*) Notice: Subject to any disclaimer, the term of this patent is extended or adjusted under 35 U.S.C. 154(b) by 544 days.

(21) Appl. No.: 16/047,262

(22) Filed: Jul. 27, 2018

(65) Prior Publication Data

US 2019/0029649 A1 Jan. 31, 2019

(30) Foreign Application Priority Data

Jul. 27, 2017 (JP) .............................. JP2017-145144

(51) Int. Cl.
*A61B 8/08* (2006.01)
*A61B 8/14* (2006.01)
*A61B 8/00* (2006.01)

(52) U.S. Cl.
CPC ............ *A61B 8/485* (2013.01); *A61B 8/5223* (2013.01); *A61B 8/5246* (2013.01); *A61B 8/14* (2013.01); *A61B 8/463* (2013.01); *A61B 8/488* (2013.01); *A61B 8/54* (2013.01)

(58) Field of Classification Search
CPC ..... A61B 8/485; A61B 8/5223; A61B 8/5246; A61B 8/14; A61B 8/54; A61B 8/488; A61B 8/463; A61B 8/461; G16H 50/30
See application file for complete search history.

(56) References Cited

U.S. PATENT DOCUMENTS

| | | | |
|---|---|---|---|
| 2006/0116579 A1* | 6/2006 | Li | A61B 8/0825 600/444 |
| 2011/0077526 A1* | 3/2011 | Zwirn | A61B 8/13 600/459 |
| 2017/0156700 A1* | 6/2017 | Honjo | G01S 7/52074 |
| 2017/0224316 A1* | 8/2017 | Shao | A61B 8/5246 |

FOREIGN PATENT DOCUMENTS

| | | |
|---|---|---|
| JP | 2014000454 A | 1/2014 |
| JP | 5635100 B2 | 12/2014 |
| JP | 2012100997 A | 5/2015 |
| JP | 2016002208 A | 1/2016 |

OTHER PUBLICATIONS

Japanese Application No. 2017-145144 filed Jul. 27, 2017—Notice of Preliminary Rejection dated Nov. 4, 2020; 8 pages.

* cited by examiner

*Primary Examiner* — Bo Joseph Peng

(57) ABSTRACT

An ultrasonic diagnostic apparatus and a method for controlling the ultrasonic diagnostic apparatus. The ultrasonic diagnostic apparatus includes: a processor for executing by a program: a first calculating function of, based on a first echo signal of first ultrasound transmitted to biological tissue in a subject to be examined, calculating a value relating to elasticity of said biological tissue; and a second calculating function of calculating a value of attenuation of ultrasound in said biological tissue; and a display device on which a first image produced based on a first two-dimensional (2D) color map CM1 is displayed, wherein said color map CM1 defines a display mode according to the value relating to elasticity of said biological tissue and the value of attenuation in said biological tissue.

7 Claims, 9 Drawing Sheets

ULTRASONIC DIAGNOSTIC APPARATUS AND METHOD

FIELD OF THE INVENTION

The present invention relates to a method and ultrasonic diagnostic apparatus for calculating a value relating to elasticity of biological tissue.

BACKGROUND OF THE INVENTION

There is known a technique of calculating a value relating to elasticity of biological tissue involving, for example, transmitting an ultrasonic pulse having a high sound pressure, i.e., push pulse, from an ultrasonic probe to biological tissue, detecting a displacement of the biological tissue induced by shear waves generated by the push pulse in the biological tissue, and calculating measurement values relating to elasticity of the biological tissue. The measurement values that are calculated include a velocity of propagation of shear waves and/or an elasticity value for biological tissue.

Once elasticity data, such as data of the velocity of propagation of shear waves or that of the elasticity value for biological tissue, has been obtained, an elasticity image having colors or the like according to the elasticity data is displayed on a display device in an ultrasonic diagnostic apparatus. The elasticity image is displayed in combination with a B-mode image in a required region defined in the B-mode image, for example.

Additional techniques of calculating a value relating to elasticity of biological tissue include one involving applying mechanical vibration to a surface of biological tissue, detecting shear waves generated by the mechanical vibration, and calculating a velocity of propagation of shear waves and/or an elasticity value for the biological tissue, or calculating distortion of the biological tissue.

BRIEF DESCRIPTION OF THE INVENTION

In a liver, for example, it is sometimes desired to make a diagnosis on a current condition of a subject to be examined taking account of the elasticity of biological tissue, and in addition, the amount of fat. The amount of fat correlates with attenuation of ultrasound, wherein the larger the amount of fat the higher attenuation while the smaller the amount of fat the lower attenuation.

The invention, in one aspect, made for solving the aforementioned problem is an ultrasonic diagnostic apparatus including: a processor for executing by a program: a first calculating function of, based on a first echo signal of first ultrasound transmitted to biological tissue in a subject to be examined, calculating a value relating to elasticity of said biological tissue; and a second calculating function of calculating a value of attenuation of ultrasound in said biological tissue; and a display device on which is displayed a first image having a display mode according to the value relating to elasticity of said biological tissue and the value of attenuation in said biological tissue, and representing said biological tissue.

The invention, in another aspect, is an ultrasonic diagnostic apparatus including: a processor for executing by a program: a first calculating function of, based on a first echo signal of first ultrasound transmitted to biological tissue in a subject to be examined, calculating a value relating to elasticity of said biological tissue; and a second calculating function of calculating a value of attenuation of ultrasound in said biological tissue; a third calculating function of calculating a first precision indicating correctness of the value relating elasticity of the biological tissue calculated by said first calculating function; and a fourth calculating function of calculating a second precision indicating correctness of the value of attenuation calculated by said second calculating function; and a display device on which is displayed a third image having a display mode according to said first precision and said second precision.

According to the invention in the one aspect described above, on a display device is displayed a first image having a display mode according to the value relating to elasticity of said biological tissue and the value of attenuation in said biological tissue, and representing said biological tissue, and therefore, it is possible to make a diagnosis taking account of in what condition and at what position both the amount of fat having correlativity with attenuation, and the elasticity are.

According to the invention in the other aspect described above, on a display device is displayed a third image having a display mode according to a first precision indicating correctness of the value relating to elasticity of biological tissue and a second precision indicating correctness of the value of attenuation of ultrasound, and therefore, it is possible to know where both or one of the value relating to elasticity of biological tissue and the value of attenuation of ultrasound are incorrect. Thus, in making a diagnosis taking account of both the amount of fat having correlativity with attenuation, and the elasticity, it is possible to know whether or not a correct diagnosis may be made.

DETAILED DESCRIPTION OF THE INVENTION

Figure 1:
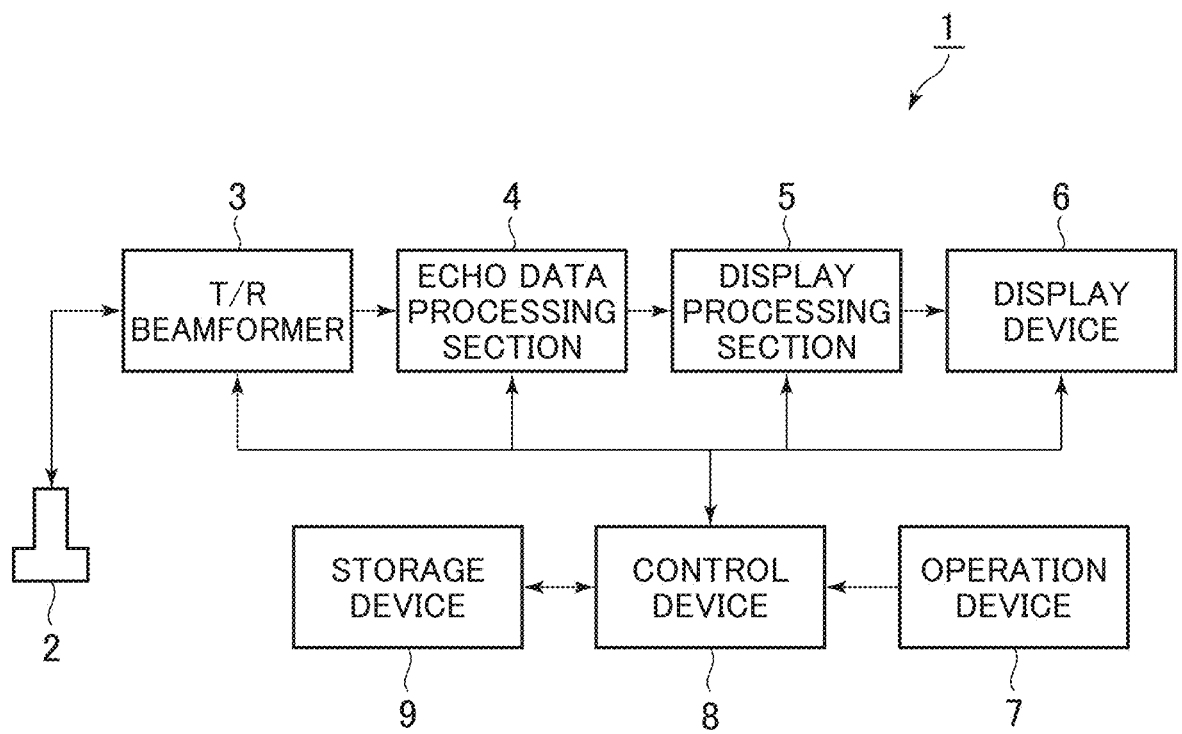
FIG. 1 A block diagram showing a general configuration of an ultrasonic diagnostic apparatus, which is an exemplary embodiment of the present invention.

To begin with, a first embodiment will be described. An ultrasonic diagnostic apparatus 1 shown in FIG. 1 comprises an ultrasonic probe 2, a transmission/reception (T/R) beamformer 3, an echo data processing section 4, a display processing section 5, a display device 6, an operation device 7, a control device 8, and a storage device 9. The ultrasonic diagnostic apparatus 1 has a configuration as a computer.

The ultrasonic probe 2 transmits ultrasound to biological tissue in a subject to be examined. In the ultrasonic probe 2, a plurality of ultrasonic transducers are arranged in an azimuthal direction, although not particularly shown. An ultrasonic pulse (push pulse) for generating shear waves in the biological tissue is transmitted by the ultrasonic probe 2. It is also by the ultrasonic probe 2 that an ultrasonic detecting pulse for detecting shear waves generated in the biological tissue by the push pulse is transmitted and an echo signal thereof is received. The ultrasonic detecting pulse is an exemplary embodiment of the first ultrasound in the present invention. The echo signal of the ultrasonic detecting pulse is an exemplary embodiment of the first echo signal in the present invention.

Moreover, it is by the ultrasonic probe 2 that an ultrasonic B-mode imaging pulse for producing a B-mode image is transmitted and an echo signal thereof is received. The ultrasonic B-mode pulse is an exemplary embodiment of the second ultrasound in the present invention. The echo signal of the ultrasonic B-mode pulse is an exemplary embodiment of the second echo signal in the present invention.

Furthermore, ultrasonic pulses for purposes other than those described above may be transmitted by the ultrasonic probe 2.

The T/R beamformer 3 drives the ultrasonic probe 2 based on a control signal from the control device 8 to transmit the aforementioned several kinds of ultrasonic pulses having predefined transmit parameters. The T/R beamformer 3 also performs signal processing, such as phased addition processing, on the echo signals of the ultrasound.

Figure 2:
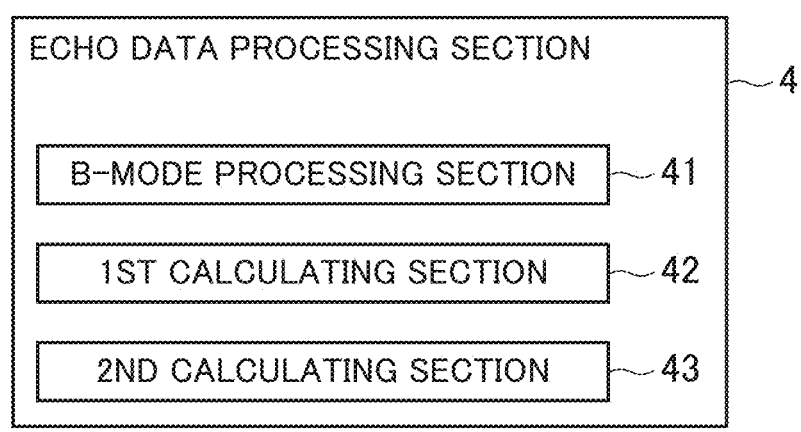
FIG. 2 A block diagram showing an exemplary configuration of an echo data processing section.

The echo data processing section 4 has a B-mode processing section 41, a first calculating section 42, and a second calculating section 43, as shown in FIG. 2. The B-mode processing section 41 performs B-mode processing, such as logarithmic compression processing and envelope detection processing, on echo data output from the T/R beamformer 3 to create B-mode data.

The first calculating section 42 calculates a velocity of propagation of the shear waves generated by the push pulse described above in the biological tissue. Specifically, the first calculating section 42 detects the shear waves based on the echo data derived from the echo signal of the ultrasonic detecting pulse and output from the T/R beamformer 3. The first calculating section 42 then calculates a velocity of propagation of the shear waves to create data representing the velocity of propagation of the shear waves. The velocity of propagation is calculated based on echo data obtained from a first display region R1, which will be discussed later. Therefore, a velocity of propagation of shear waves in the first display region R1 is calculated. The data representing the velocity of propagation is obtained for each portion corresponding to a pixel in an elasticity image, which will be discussed later. The data representing the velocity of propagation will be referred to herein as elasticity data.

The velocity of shear waves in biological tissue varies depending upon elasticity of the biological tissue. Therefore, a velocity of propagation according to elasticity of the biological tissue may be obtained in the first display region R1. The velocity of propagation of shear waves is an exemplary embodiment of the value relating to elasticity of biological tissue in the present invention. The function of calculating the velocity of propagation of shear waves by the first calculating section 42 is an exemplary embodiment of the first calculation function in the present invention.

The first calculating section 42 may calculate an elasticity value for the biological tissue (Young's modulus (in Pa: Pascal)) based on the velocity of propagation to create data representing the elasticity value as the elasticity data. The elasticity value is an exemplary embodiment of the value relating to elasticity of biological tissue in the present invention. The function of calculating the elasticity value by the first calculating section 42 is an exemplary embodiment of the first calculation function in the present invention.

The second calculating section 43 calculates a value of attenuation of ultrasound in the biological tissue. Details thereof will be discussed later. The function of calculating the value of attenuation by the second calculating section 43 is an exemplary embodiment of the second calculation function in the present invention.

Figure 3:
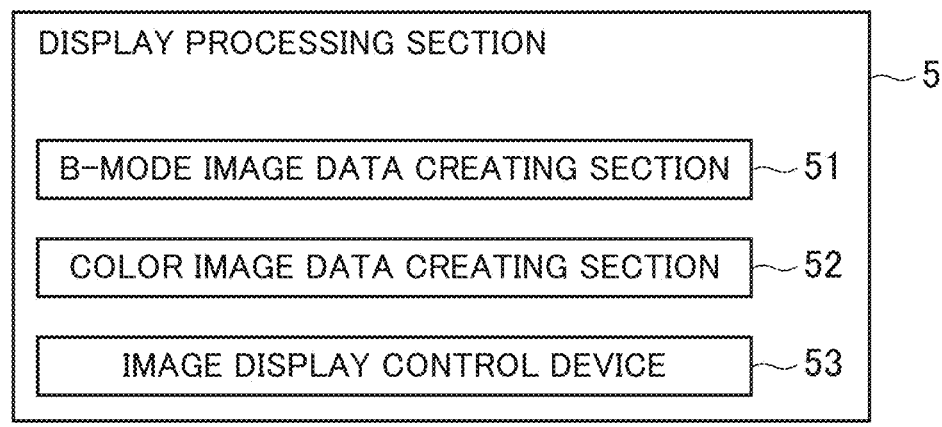
FIG. 3 A block diagram showing an exemplary configuration of a display processing section.

The display processing section 5 has a B-mode image data creating section 51, a color image data creating section 52, and an image display control device 53, as shown in FIG. 3. The B-mode image data creating section 51 creates B-mode image data by scan-converting B-mode data by a scan converter.

The color image data creating section 52 creates first color data having color information according to the value relating to elasticity of the biological tissue and the attenuation of ultrasound in the biological tissue. In this embodiment, the color image data creating section 52 creates first color data having color information according to the velocity of propagation or elasticity value calculated by the first calculating section 42, and to the value of attenuation of ultrasound calculated by the second calculating section 43. The color image data creating section 52 creates the first color data using a first two-dimensional (2D) color map CM1. Details thereof will be discussed later. Moreover, the color image data creating section 52 creates first color image data by scan-converting the first color data by the scan converter. The function of creating the first color data and first color image data in the color image data creating section 52 is an exemplary embodiment of the data creating function in the present invention.

Figure 4:
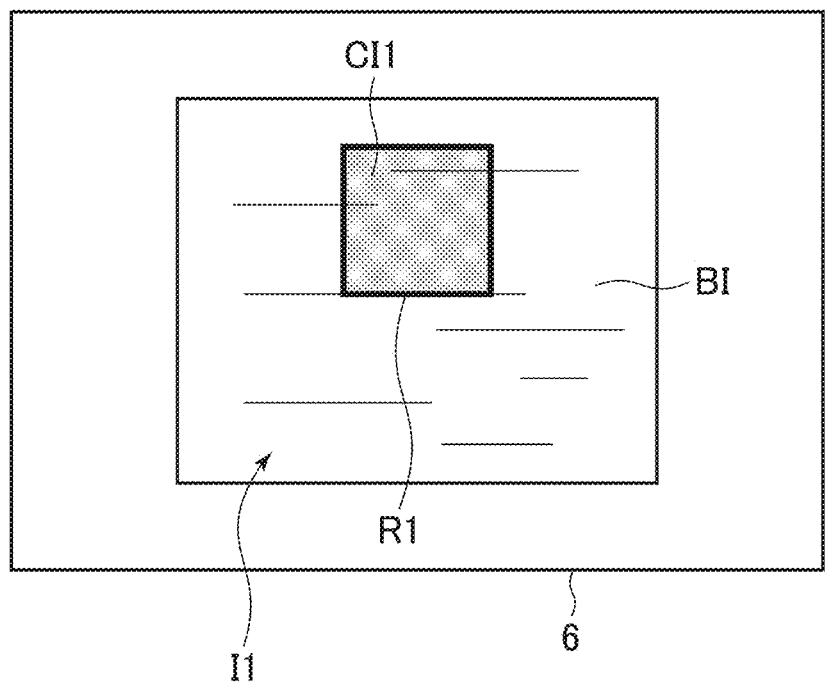
FIG. 4 A diagram showing a display device on which a combined image composed of a B-mode image and a first color image is displayed in the first embodiment.

The image display control device 53 adds the B-mode image data and first color image data together to thereby create first combined image data in which the B-mode image data and first color image data are combined together. The image display control device 53 displays a first combined image I1 based on the first combined image data on the display device 6, as shown in FIG. 4. The first combined image I1 is comprised of the B-mode image BI and first color image CI1. The first color image CI1 is displayed within the first display region R1. The first color image CI1 is a semi-transparent color image through which the B-mode image BI in the background passes. The function by the image display control device 53 is an exemplary embodiment of the image display control function in the present invention. The first color image CI is an exemplary embodiment of the first image in the present invention.

Note that the B-mode image BI is an image representing morphology of biological tissue, which is an exemplary embodiment of the second image in the present invention.

The image display control device 53 may display the B-mode image BI alone based on the B-mode image data on the display device 6.

The display device 6 is an LCD (Liquid Crystal Display), an organic EL (Electro-Luminescence) display, or the like. The display device 6 is an exemplary embodiment of the display device in the present invention.

The operation device 7 is a device for accepting an input of a command and information from the user. The operation device 7 is configured to include buttons, a keyboard, etc. for accepting an input of a command and information from the user, and to further include a pointing device, such as a trackball, and the like.

The control device 8 is a processor such as a CPU (Central Processing Unit). The control device 8 loads thereon programs stored in the storage device 9 to control several sections in the ultrasonic diagnostic apparatus 1. For example, the control device 8 loads thereon programs stored in the storage device 9, and executes functions of the T/R beamformer 3, echo data processing section 4, and display processing section 5 by the loaded programs.

The control device 8 may execute all of the functions of the T/R beamformer 3, all of the functions of the echo data processing section 4, and all of the functions of the display processing section 5 by the programs, or execute only part of the functions by the programs. In the case that the control device 8 executes only part of the functions, the remaining functions may be executed by hardware, such as circuitry.

The functions of the T/R beamformer 3, echo data processing section 4, and display processing section 5 may be implemented by hardware, such as circuitry.

The storage device 9 includes non-transitory storage media and transitory storage media. The non-transitory storage media are non-volatile storage media, such as HDD (Hard Disk Drive) and ROM (Read Only Memory), for example. The non-transitory storage media may include portable storage media, such as CD (Compact Disk) and DVD (Digital Versatile Disk).

The transitory storage media are volatile storage media, such as RAM (Random Access Memory).

The programs executed by the control device 8 are stored in a non-transitory storage medium, such as HDD or ROM, constituting the storage device 9. The programs may also be stored in a non-transitory storage medium having portability, such as CD or DVD, constituting the storage device 9.

In the storage device 9 is also stored the first 2D color map CM1.

Figure 5:
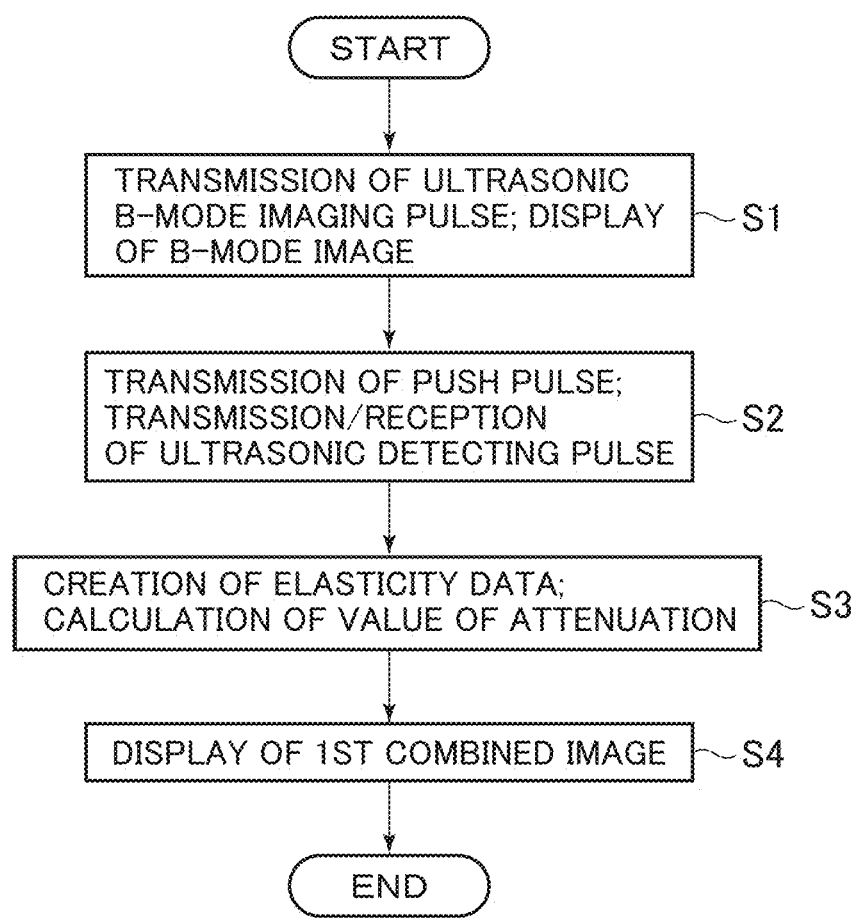
FIG. 5 A flow chart showing an operation for displaying a first combined image in the ultrasonic diagnostic apparatus in the first embodiment.

Next, an operation for displaying the combined image in the ultrasonic diagnostic apparatus 1 of the present embodiment will be described with reference to the flow chart in FIG. 5.

Figure 6:
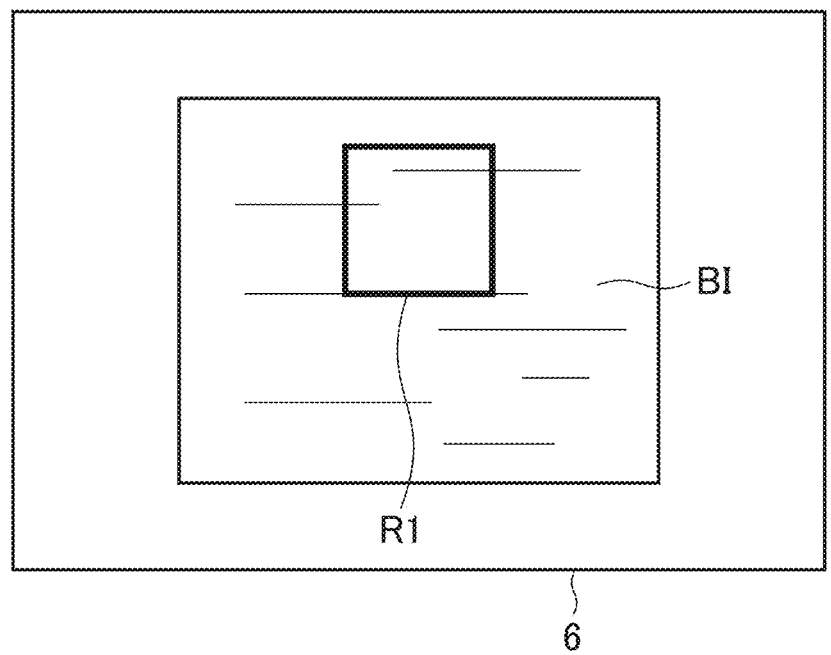
FIG. 6 A diagram showing the display device on which a B-mode image is displayed, wherein a region to be displayed is defined in the B-mode image.

First, at Step S1, the ultrasonic probe 2 transmits an ultrasonic B-mode imaging pulse to biological tissue in a subject to be examined, and receives an echo signal thereof. Then, based on B-mode image data created based on the echo signal, the image display control device 53 displays a B-mode image BI, as shown in FIG. 6. Once the B-mode image BI has been displayed, the user uses the operation device 7 to define a first display region R1 in the B-mode image BI. The first display region R1 is defined in a region in which a first color image CI1 is desired to be displayed.

Next, at Step S2, the ultrasonic probe 2 transmits a push pulse to the biological tissue. For example, the transmission of a push pulse may be performed once the operation device 7 has accepted an input by the operator. After the push pulse has been transmitted, the ultrasonic probe 2 transmits an ultrasonic detecting pulse to the biological tissue, and receives an echo signal thereof.

Next, at Step S3, the first calculating section 42 calculates a value relating to elasticity of the biological tissue based on the echo signal of the ultrasonic detecting pulse to create elasticity data. The first calculating section 42 here calculates an elasticity value for the biological tissue. Moreover, the second calculating section 43 calculates a value of attenuation of ultrasound in the biological tissue.

The calculation of a value of attenuation will be described. The second calculating section 43 calculates an amount of attenuation of the echo signal of the ultrasonic detecting pulse, for example, as the value of attenuation for the biological tissue. Alternatively, the second calculating section 43 may calculate an amount of attenuation of the echo signal of the ultrasonic B-mode imaging pulse transmitted at Step S1 as the value of attenuation in the biological tissue. A technique of calculating the amount of attenuation that is used is a commonly known technique involving approximating echo signals toward a straight line, and calculating a slope (in a depth direction) of the straight line.

The second calculating section 43 may calculate a global value of attenuation in the first display region R1. Specifically, the second calculating section 43 may calculate one value of attenuation representative of attenuation of ultrasound in a region in the biological tissue corresponding to the region in which the first color image CI1 is to be displayed, which will be discussed later; in other words, it may calculate one value of attenuation for the first display region R1. In this case, the second calculating section 43 may calculate, for example, an amount of attenuation in a portion corresponding to the first display region R1 in one acoustic line along which the ultrasonic detecting pulse or ultrasonic B-mode imaging pulse is transmitted/received. The second calculating section 43 may also calculate a mean amount of attenuation in a plurality of acoustic lines in the first display region R1. It will be easily recognized that in the first display region R1, the ultrasonic detecting pulse or ultrasonic B-mode imaging pulse is transmitted/received in a plurality of acoustic lines.

The second calculating section 43 may also calculate a local value of attenuation in the first display region R1. Specifically, the second calculating section 43 may calculate a value of attenuation for each of a plurality of portions of the region in the biological tissue corresponding to the region in which the first color image CI1 is to be displayed, in other words, it may calculate a plurality of values of attenuation for the first display region R1. In this case, the second calculating section 43 calculates, for example, amounts of attenuation in a plurality of portions in each of the plurality of acoustic lines along which the ultrasonic detecting pulse or ultrasonic B-mode imaging pulse is transmitted/received.

At Step S4, the image display control device 53 displays the first combined image I1 on the display device 6 as shown in FIG. 4 described earlier. More specifically, the color image data creating section 52 first creates first color data having color information according to the elasticity value and the value of attenuation for the biological tissue. The color image data creating section 52 creates the first color data based on the first 2D color map CM1 shown in FIG. 7.

Figure 7:
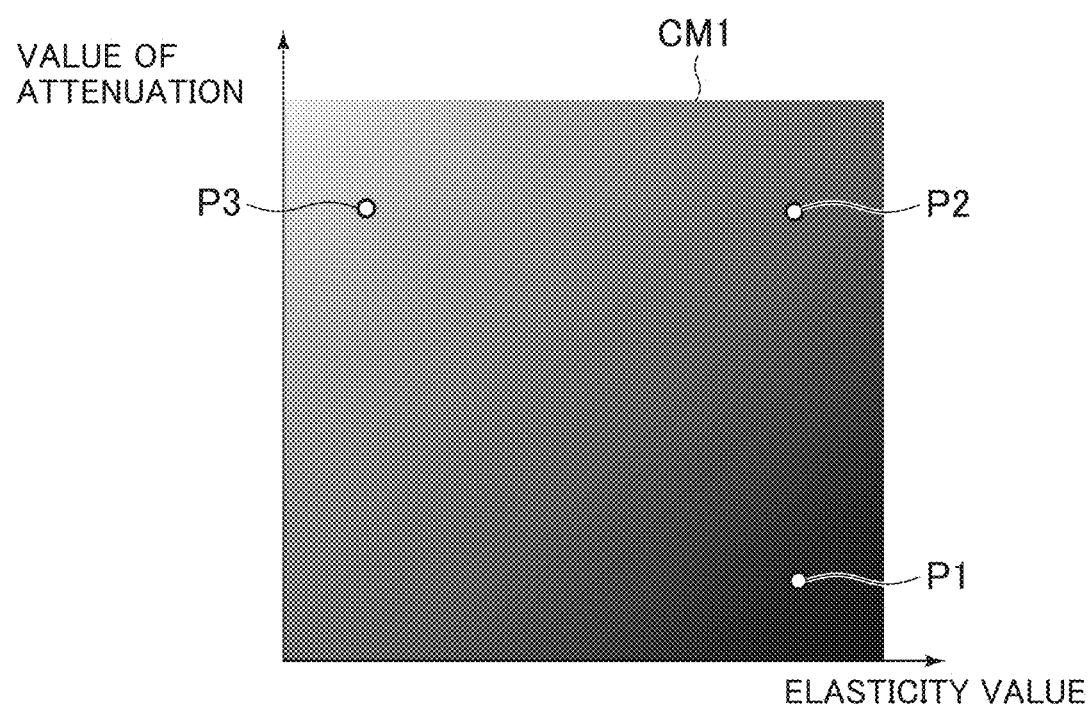
FIG. 7 A diagram showing an exemplary first two-dimensional (2D) color map.

The first 2D color map CM1 has color information according to the elasticity value and the value of attenuation for the biological tissue. The color information is information consisting of hue, chroma, and lightness. The first 2D color map CM1 in FIG. 7 shows the color information in grayscale. The first 2D color map CM1 is an exemplary embodiment of the first two-dimensional map in the present invention. The color information is an exemplary embodiment of the display mode in the present invention.

By using the first 2D color map CM1, first color data having different color information is created for the same elasticity value for the biological tissue and a different value of attenuation, and first color data having different color information is created for the same value of attenuation and a different elasticity value for the biological tissue. For example, in the first 2D color map CM1, a point P1 indicates relatively hard biological tissue (a relatively large elasticity value) and a relatively small amount of fat (a relatively small amount of attenuation). A point P2 indicates relatively hard biological tissue (a relatively large elasticity value, which is the same as that at the point P1) and a relatively large amount of fat (a relatively large amount of attenuation). A point P3 indicates relatively soft biological tissue (a relatively small elasticity value) and a relatively large amount of fat (a relatively large amount of attenuation, which is the same as that at the point P2).

Figure 8:
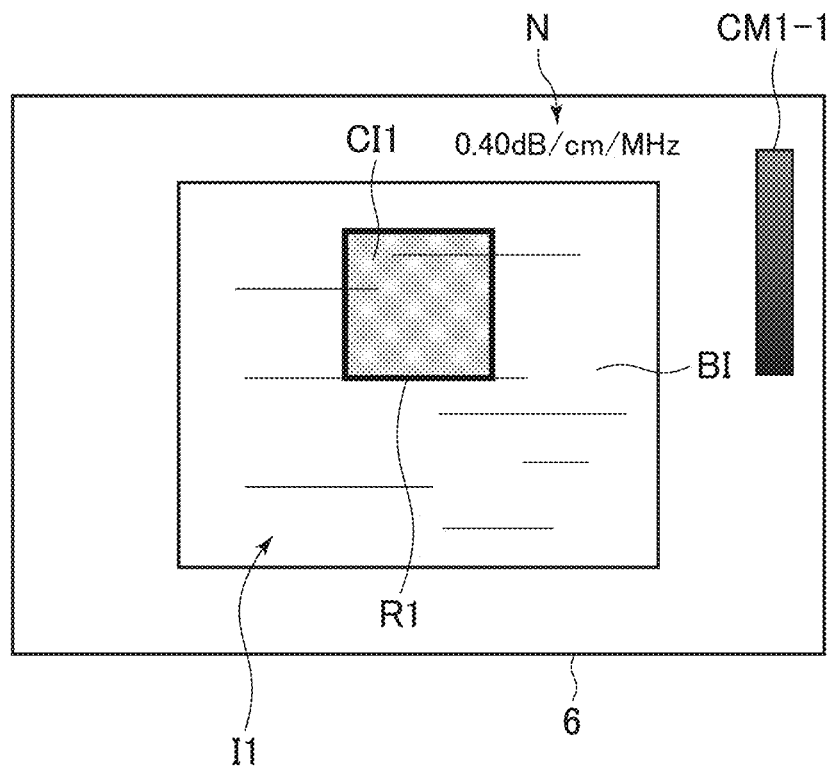
FIG. 8 A diagram showing the display device on which a global value of attenuation is displayed.
Figure 9:
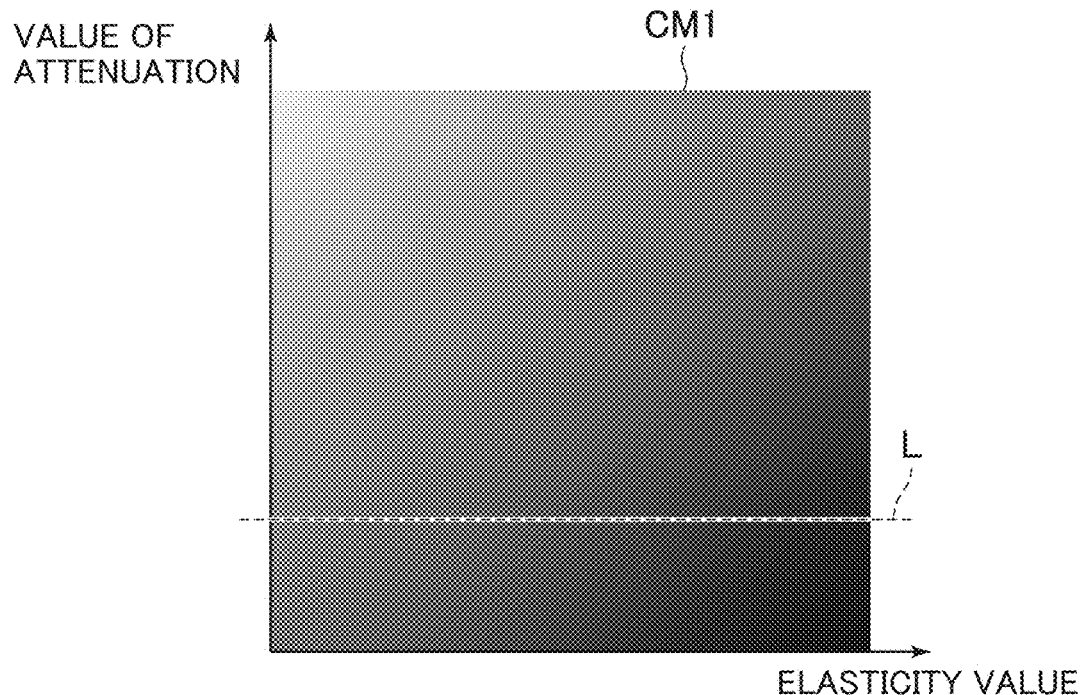
FIG. 9 An explanatory diagram showing a dashed line corresponding to one value of attenuation in the first 2D color map.

When the global value of attenuation, i.e., one representative value of attenuation in the first display region R1, is calculated, the image display control device 53 may display a figure N designating the value of attenuation on the display device 6, as shown in FIG. 8. In this case, the image display control device 53 may display a one-dimensional (1D) color map CM1-1 for the one representative value of attenuation on the display device 6. The 1D color map CM1-1 is a color map on a dashed line L in the first 2D color map CM1, for example, shown in FIG. 9.

When the one representative value of attenuation is calculated and the elasticity value is calculated on a pixel-by-pixel basis in the first color image CI1, color information according to the elasticity value is selected on a pixel-by-pixel basis from among color information according to the one representative value of attenuation.

When local values of attenuation, i.e., a plurality of values of attenuation in the first display region R1, are calculated, on the other hand, the image display control device 53 may display a 2D color map CM on the display device 6, although not particularly shown.

When a plurality of values of attenuation are calculated but the value of attenuation is not calculated on a pixel-by-pixel basis in the first color image CI, and at the same time the elasticity value is calculated on a pixel-by-pixel basis, then, for each pixel in each of a plurality of portions for which a value of attenuation is calculated, color information according to the elasticity value is selected from among color information according to the value of attenuation calculated for that portion.

After creating the first color data, the color image data creating section 52 creates first color image data based on the first color data. Then, the image display control device 53 displays a first combined image I1 comprised of a B-mode image BI and a first color image CI1 in the first display region R1 based on the B-mode image data and first color image data.

The first color image CI1 has color information according to the elasticity value and the value of attenuation, and represents the biological tissue (part of it here). By such a first color image CI1 being displayed, a diagnosis may be made taking account of in what condition and at what position in the first display region R1 both the amount of fat and the elasticity are.

Figure 10:
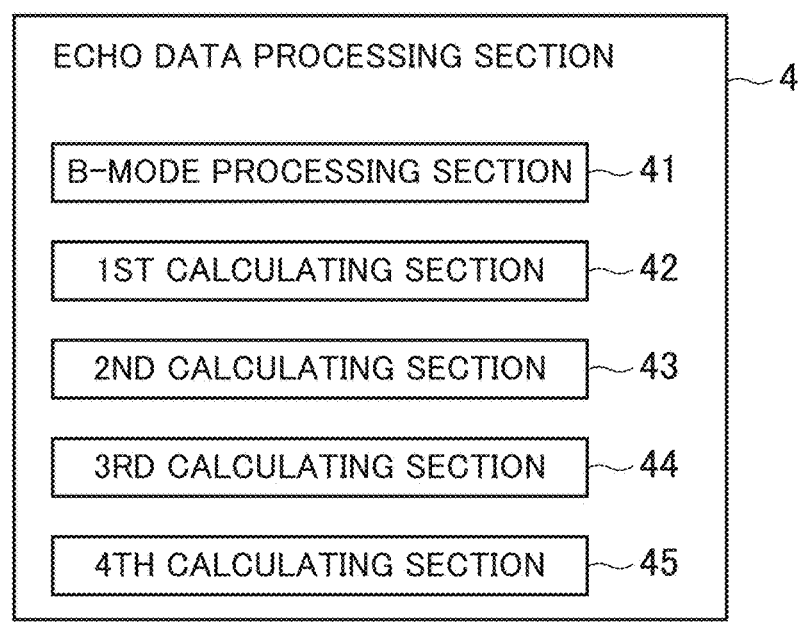
FIG. 10 A block diagram showing another exemplary configuration of the echo data processing section.

Next, a variation of the first embodiment will be described. In this variation, the echo data processing section 4 has the B-mode processing section 41, first calculating section 42, second calculating section 43, and in addition, a third calculating section 44 and a fourth calculating section 45, as shown in FIG. 10.

The third calculating section 44 calculates a first precision indicating correctness of the value relating to elasticity of the biological tissue calculated by the first calculating section 42. The function of the third calculating section 44 is an exemplary embodiment of the third calculation function in the present invention.

An example of calculation of the first precision will be described. The first precision is a value indicating a degree of how correctly the value relating to elasticity of the biological tissue reflects elasticity of the biological tissue. As described in Japanese Patent Application KOKAI No. 2016-67399, for example, the third calculating section 44 performs cross-correlation calculation between waveforms of the temporal change of shear wave-induced displacement of biological tissue at two points in a direction of propagation of shear waves, and obtains a correlation coefficient therefrom as the first precision. Therefore, the smaller the value of the first precision, the poorer the correctness of the value relating to elasticity of the biological tissue. Note that the waveform of the temporal change of shear wave-induced displacement of biological tissue is obtained based on the echo signal by the ultrasonic detecting pulse.

The fourth calculating section 45 calculates a second precision indicating correctness of the value of attenuation calculated by the second calculating section 43. The function of the fourth calculating section 45 is an exemplary embodiment of the fourth calculation function in the present invention.

An example of calculation of the second precision will be described below. The fourth calculating section 45 calculates as the second precision a precision of approximation of the echo signals toward a straight line when the second calculating section 42 calculates a value of attenuation. The smaller the value of the second precision, the poorer the correctness of the value of attenuation.

In this variation, the image display control device 53 performs control not to display the first color image CI1 in the case that one of a first condition imposed regarding the first precision and a second condition imposed regarding the second precision is not met. The function of the image display control device 53 is an exemplary embodiment of the image display control function in the present invention.

The first condition is, for example, that the value of the first precision calculated by the third calculating section 43 should be equal to or greater than a threshold set for the value of the first precision. The second condition is, for example, that the value of the second precision calculated by the fourth calculating section 45 should be equal to or greater than a threshold set for the value of the second precision. Therefore, when either of the case that the value of the first precision is less than the threshold or the case that the value of the second precision is less than the threshold is met, the image display control device 53 does not display the first color image CI1 in a frame giving the elasticity value at the first precision and the value of attenuation at the second precision.

Figure 11:
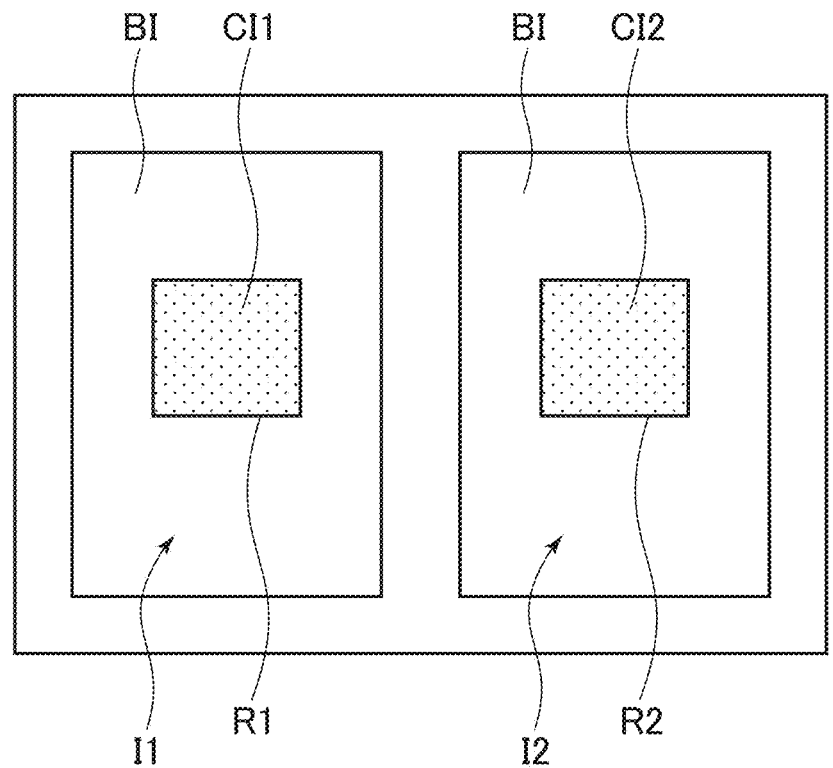
FIG. 11 A diagram showing the display device on which a combined image composed of a B-mode image and a second color image is displayed in a second embodiment.

The ultrasonic diagnostic apparatus 1 in the second embodiment has the configuration shown in FIG. 1. The echo data processing section 4 has the configuration shown in FIG. 10. In this embodiment, a second color image CI2 having a display mode according to a first precision and a second precision is displayed on the display device 6 as shown in FIG. 11.

Figure 12:
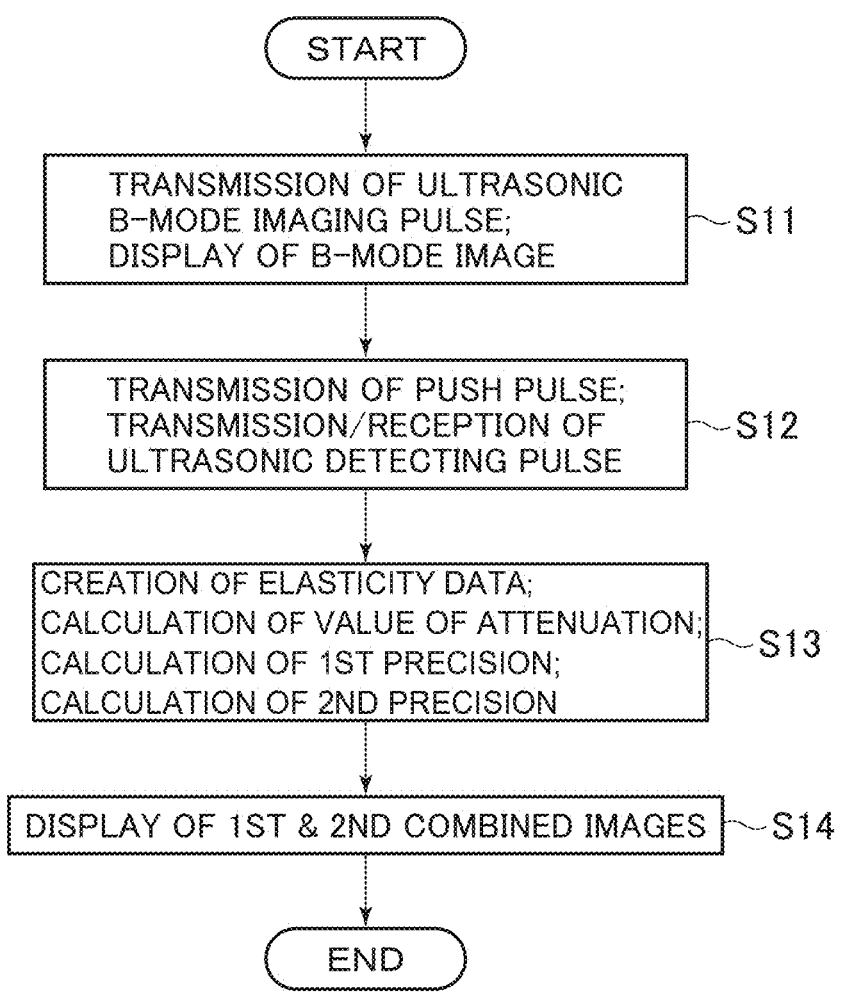
FIG. 12 A flow chart showing an operation for displaying first and second combined images in the ultrasonic diagnostic apparatus in the second embodiment.

In this embodiment, processing according to the flow chart in FIG. 12 is executed. In the flow chart in FIG. 12, processing at Steps S11 and S12 is similar to that in Steps S1 and S2. At Step S13, creation of elasticity data and calculation of a value of attenuation are performed as in Step S3. Moreover, at Step S13, calculation of a first precision by the third calculating section 44 and calculation of a second precision by the fourth calculating section 45 are performed.

At Step S14, in addition to the first combined image I1, a second combined image I2 comprised of the B-mode image BI and a second color image CI2 is displayed.

Creation of the second color image CI2 will be described. In this embodiment, the color image data creating section 52 creates the first color data, and in addition, second color data having color information according to the first precision and second precision. The color image data creating section 52 creates the second color data based on a second 2D color map CM2 shown in FIG. 13.

Figure 13:
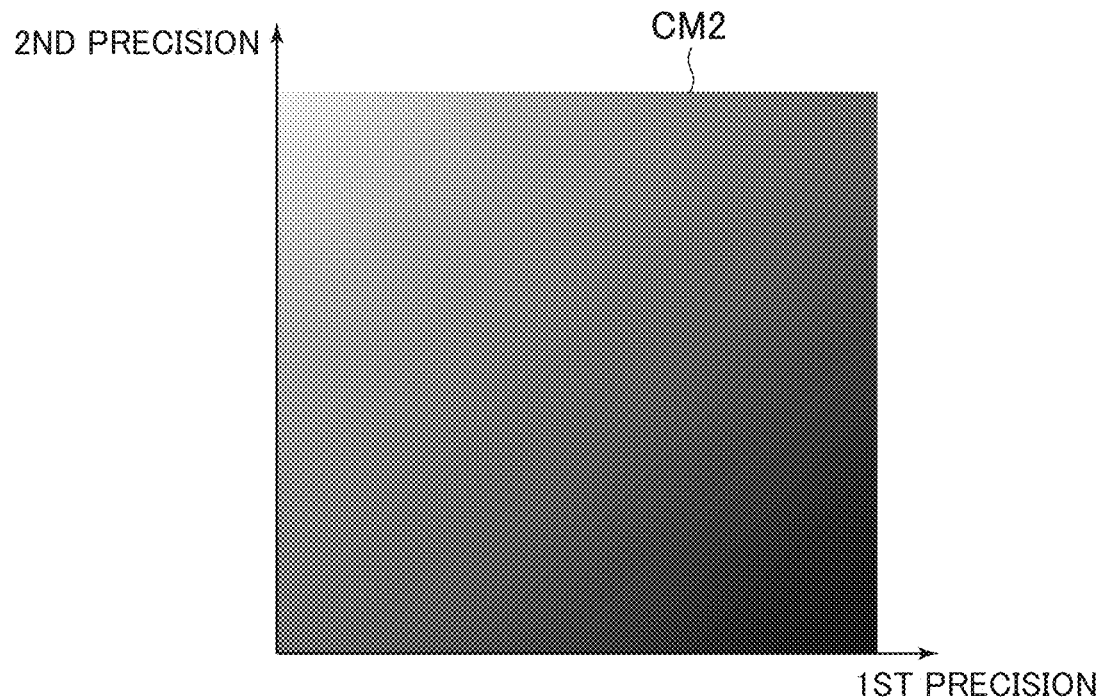
FIG. 13 A diagram showing an exemplary second 2D color map.

The second 2D color map CM2 has color information according to the value of the first precision and that of the second precision. The color information is information consisting of hue, chroma, and lightness. Again, the second 2D color map CM2 in FIG. 13 shows the color information in grayscale. The second 2D color map CM2 is an exemplary embodiment of the second two-dimensional map in the present invention. The color information is an exemplary embodiment of the display mode in the present invention.

After creating the second color data, the color image data creating section 52 scan-converts the second color data by the scan converter to create second color image data. The function of creating the second color data and second color image data in the color image data creating section 52 is an exemplary embodiment of the data creating function in the present invention.

The image display control device 53 displays a second combined image I2 comprised of a B-mode image BI and a second color image CI2 on the display device 6 based on the B-mode image data and second color image data. The second color image CI2 is displayed in a second display region R2 defined in the B-mode image BI. The second color image CI2 is an exemplary embodiment of the third image in the present invention. The image display control device 53 displays the second combined image I2 and the first combined image I1 side by side, as shown in FIG. 11.

The B-mode image BI constituting the second combined image I2 may be the same as that constituting the first combined image I1. Moreover, ultrasound transmission/reception for producing the B-mode image BI constituting the second combined image I2 may be performed separately from that for producing the B-mode image BI constituting the first combined image I1.

The image display control device 53 may switchably display the first combined image I1 and second combined image I2 on the display device 6. In this case, the image display control device 53 may switch between the first combined image I1 and second combined image I2 when, for example, the operation device 7 has accepted an input by the operator.

The second color image CI2 has color information according to the first precision and second precision. By such a second color image CI2 being displayed, it is possible to know where both or one of the value relating to elasticity of biological tissue and the value of attenuation of ultrasound are incorrect. Thus, in making a diagnosis taking account of both the amount of fat having correlativity with attenuation, and the elasticity, it is possible to know whether or not a correct diagnosis may be made.

Next, a variation of the second embodiment will be described. In this variation, the first combined image I1 is not displayed and the second combined image I2 is displayed alone.

While the present invention has been described with reference to the embodiments, it will be easily recognized that the present invention may be practiced with several modifications in the scope without changing the spirit thereof. While in the embodiments described above, the second calculating section 43 calculates the amount of attenuation of the echo signal of the ultrasonic detecting pulse or that of the echo signal of the ultrasonic B-mode imaging pulse, an echo signal for which the amount of attenuation is calculated is not limited thereto. For example, aside from the ultrasonic detecting pulse for detecting shear waves and the ultrasonic B-mode pulse, an ultrasonic pulse for measuring attenuation in biological tissue may be transmitted. The ultrasonic pulse for measuring attenuation is an exemplary embodiment of the third ultrasound. Moreover, an echo signal of the ultrasonic pulse for measuring attenuation is an exemplary embodiment the third echo signal. In this case, the second calculating section 43 calculates a value of attenuation of the echo signal of the ultrasonic pulse for measuring attenuation.

Figure 14:
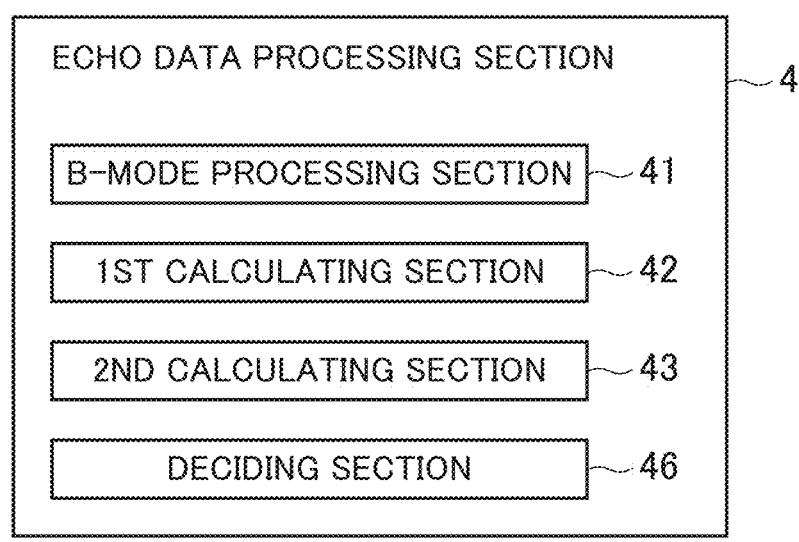
FIG. 14 A block diagram showing still another exemplary configuration of the echo data processing section.

Moreover, the echo data processing section 4 may have a deciding section 46, as shown in FIG. 14. The deciding section 46 decides a precision of matching in position between a cross section to which the ultrasonic detecting pulse is transmitted and that to which the ultrasonic B-mode pulse is transmitted based on a degree of correlation between echo signals of the ultrasonic detecting pulse and the ultrasonic B-mode pulse. The deciding section 46 may decide a precision of matching in position between the cross section to which the ultrasonic detecting pulse is transmitted and that to which the ultrasonic pulse for measuring attenuation is transmitted based on a degree of correlation between echo signals of the ultrasonic detecting pulse and the ultrasonic pulse for measuring attenuation. Furthermore, the deciding section 46 may decide a precision of matching between a cross section to which the ultrasonic B-mode pulse is transmitted and that to which the ultrasonic pulse for measuring attenuation is transmitted based on a degree of correlation between echo signals of the ultrasonic B-mode pulse and the ultrasonic pulse for measuring attenuation. The deciding function by the deciding section 46 is an exemplary embodiment of the deciding function in the present invention.

It may be contemplated that the deciding section 46 calculates the degree of correlation for each of a plurality of acoustic lines in one frame, and decides the precision of matching based on a mean value thereof. Moreover, the deciding section 46 may decide the precision of matching by calculating the degree of correlation for any one of the acoustic lines in one frame.

The image display control device 53 may display a result of the decision by the deciding section 46 on the display device 6. For example, the result of the decision by the deciding section 46 is displayed as a numeric value indicating the precision of matching according to the degree of correlation on the display device 6.

The echo data processing section 4 shown in FIG. 10 may further have the deciding section 46, although not particularly shown.

The technique of calculating the first precision and second precision described above is exemplary, and the third calculating section 44 and fourth calculating section 45 may calculate the first precision and second precision according to any other technique. For example, the fourth calculating section 44 may calculate a variance of the signal intensity of the echo signal as the second precision.

Moreover, the technique of obtaining an value relating to elasticity of biological tissue in a subject is not limited to that described above. For example, it may be contemplated that mechanical vibration is applied to a surface of biological tissue, shear waves generated by the mechanical vibration are detected, and the velocity of propagation of the shear waves and/or the elasticity value for the biological tissue is calculated.

Furthermore, the value relating to elasticity of biological tissue is not limited to the velocity of propagation or elasticity value. For example, a distortion of biological tissue may be obtained as the value relating to elasticity of biological tissue.

We claim:

1. An ultrasonic diagnostic apparatus comprising:
    an ultrasonic probe;
    a display device; and
    a processor configured to:
        drive the ultrasonic probe to transmit a plurality of B-mode imaging pulses and a plurality of shear wave detecting pulses to biological tissue in a subject;
        control the ultrasonic probe to receive a first plurality of echoes from the plurality of B-mode imaging pulses and a second plurality of echoes from the shear wave detecting pulses;
        generate a B-mode image based a first plurality of echoes;
        calculate at least one value of attenuation in a region of the biological tissue based on one or both of the first plurality of echoes or the second plurality of echoes;
        calculate a plurality of elasticity values for the region of the biological tissue based on the second plurality of echoes;
        identify a plurality of colors corresponding to the plurality of elasticity values and the at least one value of attenuation based on a two-dimensional color map, wherein the two-dimensional color map defines color according to both value of attenuation and elasticity value, and wherein the processor is configured to identify the plurality of colors using the two-dimensional color map based on the at least one value of attenuation in the region and the plurality of elasticity values for the region;
        create a first color image of the region based on the plurality of identified colors;
        combine the B-mode image and the first color image to create a combined image; and
        display the combined image on the display device.

2. The ultrasonic diagnostic apparatus of claim 1, wherein the at least one value of attenuation is a global value of attenuation in the region of the biological tissue, and wherein the region of the biological tissue corresponds to the first color image, and wherein the processor is configured to create the first color image by identifying each of the plurality of colors in the two-dimensional color map on a pixel-by-pixel basis, wherein each of the plurality of colors corresponds to the global value of attenuation and the elasticity value calculated for each of a plurality of pixels in the first color image.

3. The ultrasonic diagnostic apparatus of claim 1, wherein the at least one value of attenuation comprises a plurality of values of attenuation, wherein each of the plurality of values of attenuation is calculated for a different one of a plurality of portions of the region in the biological tissue, wherein the region of the biological tissue corresponds to the first color image, wherein the processor is configured to create the first color image by identifying a plurality of colors in the two-dimensional color map on a pixel-by-pixel basis, wherein the processor is configured to identify the plurality of colors based on a corresponding one of the plurality of values of attenuation and a corresponding one of the plurality of elasticity values for each of a plurality of pixels in the first color image.

4. The ultrasonic diagnostic apparatus as recited in claim 1, wherein: said processor is further configured to determine a precision of matching in position between a first cross section to which the plurality of B-mode imaging pulses is transmitted and a second cross section to which the plurality of shear wave detecting pulses is transmitted based on a degree of correlation between the first plurality of echoes and the second plurality of echoes.

5. The ultrasonic diagnostic apparatus as recited in claim 1, wherein said processor is further configured to:
    calculate a first precision, wherein the first precision is a value indicating a correctness of the plurality of elasticity values;
    calculate a second precision, wherein the second precision is a value indicating a correctness of the at least one value of attenuation;
    and wherein the processor is configured not to display the first color image if either the first precision is below a first threshold or the second precision is below a second threshold.

6. The ultrasonic diagnostic apparatus as recited in claim 5, wherein the processor is further configured to:
    identify an additional plurality of colors based on a second two-dimensional color map, wherein the second two-dimensional color map defines color according to both the first precision and the second precision;
    create a second color image based on the calculated first precision, the calculated second precision, and the second two-dimensional color map;
    combine the B-mode image and the second color image to create a second combined image;
    display the second combined image on the display device.

7. The ultrasonic diagnostic apparatus as recited in claim 6, wherein the processor is configured to perform one or both of the following:
    cause the display device to switch between displaying the first combined image and the second combined image; or
    cause the display device to display the first combined image and the second combined image side by side.

* * * * *